(12) United States Patent
Donitzky

(10) Patent No.: US 6,805,694 B2
(45) Date of Patent: Oct. 19, 2004

(54) LASER SYSTEM FOR CORNEAL GRAFTING

(75) Inventor: Christof Donitzky, Eckental (DE)

(73) Assignee: WaveLight Laser Technologie AG, Erlangen (DE)

( * ) Notice: Subject to any disclaimer, the term of this patent is extended or adjusted under 35 U.S.C. 154(b) by 139 days.

(21) Appl. No.: 10/141,902

(22) Filed: May 8, 2002

(65) Prior Publication Data

US 2002/0173779 A1 Nov. 21, 2002

(30) Foreign Application Priority Data

May 18, 2001 (DE) .......................... 101 24 358

(51) Int. Cl.⁷ .............................................. A61B 9/007
(52) U.S. Cl. .............................. 606/5; 606/10; 128/898
(58) Field of Search .............................. 606/5, 10–13; 623/5.15; 128/898

(56) References Cited

U.S. PATENT DOCUMENTS

| | | | |
|---|---|---|---|
| 4,842,599 A | * | 6/1989 | Bronstein .................. 623/5.15 |
| 4,907,586 A | | 3/1990 | Bille et al. |
| 5,624,437 A | | 4/1997 | Freeman et al. |
| 5,647,865 A | | 7/1997 | Swinger |
| 5,984,916 A | | 11/1999 | Lai |
| 5,993,438 A | | 11/1999 | Juhasz et al. |
| 6,110,166 A | * | 8/2000 | Juhasz .......................... 606/10 |

FOREIGN PATENT DOCUMENTS

| | | |
|---|---|---|
| EP | 1 138 291 A2 | 10/2001 |
| EP | 1 138 291 | 10/2001 |
| WO | WO 93/08877 | 5/1993 |
| WO | WO 94/09849 | 5/1994 |

* cited by examiner

Primary Examiner—David M. Shay
(74) Attorney, Agent, or Firm—Haynes and Boone, LLP

(57) ABSTRACT

A laser system serves for corneal grafting by photodisruptive laser cutting. To this end, short laser pulses within the range from 1 fs to 10 ns are positioned and guided in the cornea in such a way that the foci (20) of the laser pulses describe an incision path in the cornea (12) that exhibits an undercut, so that a seal between the juxtaposed surfaces of the implant and of the residual cornea arises between a donor implant and the recipient cornea which is promoted by the overpressure of the eye

42 Claims, 1 Drawing Sheet

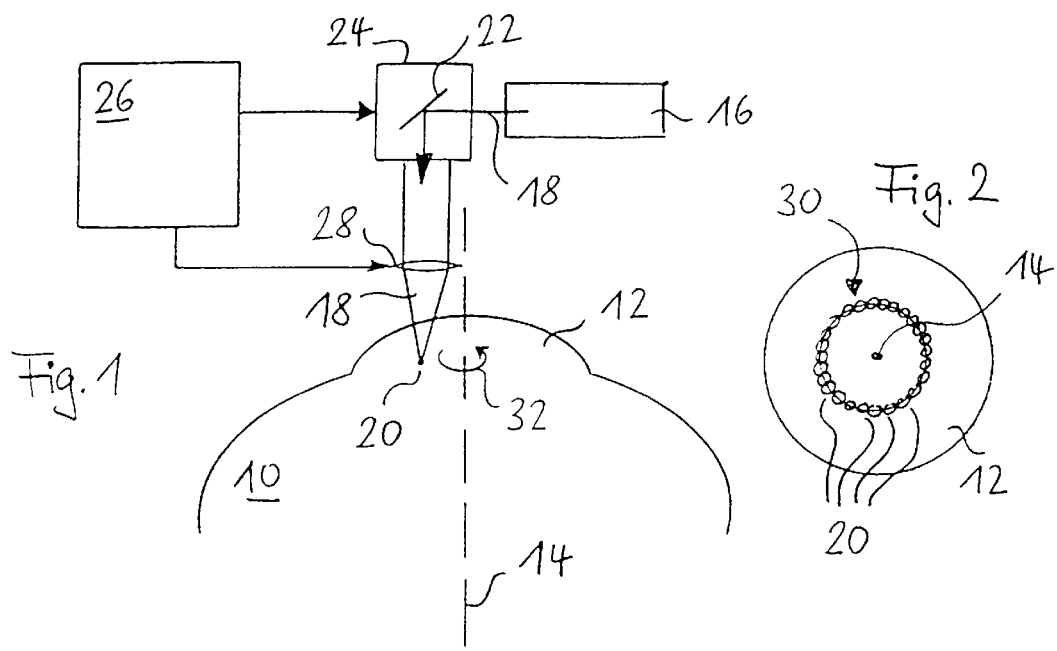
Fig. 1
Fig. 2
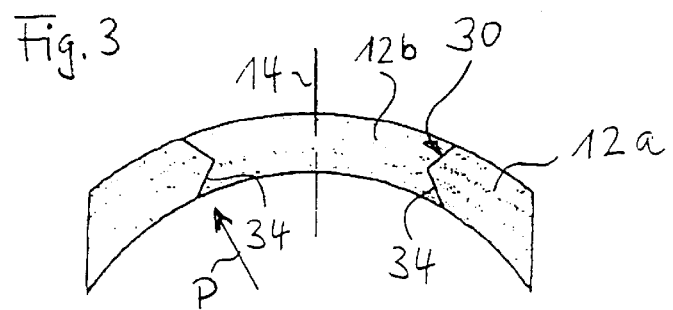
Fig. 3
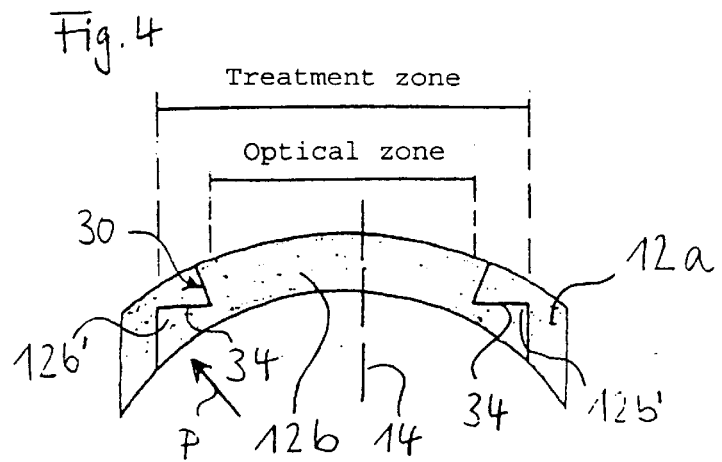
Fig. 4

LASER SYSTEM FOR CORNEAL GRAFTING

This application claims priority to German Patent Application No. 101 24 358.8, filed May 18, 2001.

The invention relates to a laser system for ophthalmic surgery, in particular for corneal grafting.

Grafting of a part of the human cornea may be indicated for a variety of reasons. For example, in the case of so-called keratoconus an irregular change occurs in the shape of the cornea, so that the optical imaging suffers too severely. Corneal grafting may also become necessary in the case of extreme clouding of the cornea as a result of, for example, loss of endothelial cells, infections, ulcers, hereditary diseases or scarring.

In a corneal grafting operation the central part of the diseased cornea in the region of the optical axis is removed surgically and a healthy donor graft is inserted.

Removal of the recipient cornea and of the donor cornea is undertaken in the state of the art by so-called trepanation. Mechanical instruments, in particular a so-called manual trepan or motorized trepan, are employed for this purpose in the state of the art. Such trepans according to the state of the art enable removal of disc-shaped corneal segments. The known trepans comprise a circular cylindrical hollow body which is ground at the lower end to form a sharp cutting surface. The diameter of the circular ground edge corresponds roughly to the diameter of the central corneal segment to be excised. In this connection, care has to be taken to ensure that the endothelium is traumatised as little as possible. A further important aspect in corneal grafting is a watertight closure of the wound.

Mechanical corneal surgery with a trepan has the disadvantage, firstly, that the geometrical structure of the excised corneal segment is defined by reason of the predetermined ground edge; by reason of the circular cylindrical configuration of the trepan only circular cylindrical segments are capable of being cut. The tendency towards deflection of the incision in the lamellar tissue depending on the curvature of the cornea also causes problems with regard to precise reproducibility of the incision. Once a trepan has been applied, only the depth of the incision can be controlled. The state of the art in trepan incision is familiar with a variety of processes for this purpose, for example the use of punches in the trepan.

A principal problem in corneal grafting is the liquid-tight closure of the wound. In the state of the art the corneal graft is fixed by the placement of a suture after successful implantation. The suture typically remains in the recipient cornea for a period of up to one year. Such a suture is not only very elaborate, it can also lead to various complications; in particular it can bring about an incorrect optical position of the donor graft or even an insufficient liquid seal. The suture can also change the optical properties of the imaging system constituted by the eye; for example, distortions in the cornea can be induced by the suture, which can lead to an astigmatism.

The liquid seal is a fundamental problem. In the eyeball the human eye has a relative overpressure of about 15 mmHg in the normal case.

The object underlying the invention is to provide means with which corneal grafting can be performed better with regard to the problems of the state of the art outlined above.

For this purpose the invention provides a laser system having the features of claim 1.

A laser system of such a type enables corneal grafting using so-called photodisruptive laser cutting.

The generation of extremely short laser pulses has recently made it possible, in ophthalmological surgery in particular, to separate a corneal lobule without mechanical cutting means by focusing of the laser pulses in the interior of the cornea, for example within the scope of LASIK treatment. Short laser pulses within the nanosecond to femtosecond range have such high power outputs that, with suitable focusing, the biological material can be "cut" in its interior without internal thermal effects or such like arising.

By virtue of the undercut in the "incision" of the cornea which is obtained in accordance with the invention, a self-sealing is obtained, since the aforementioned relative overpressure within the eye brings about full contiguity of the implant with the residual cornea of the recipient. Moreover, the shape of the incision that is obtained in accordance with the invention has the advantage that it also promotes the optical centering of the donor implant in the recipient cornea. By this means, the suturing of the inserted implant is also reduced to a minimum and the disadvantages caused thereby are very largely avoided.

According to a preferred configuration of the invention the undercut is zigzag-shaped. The undercut is so designed that, viewed from the interior of the eye, a part of the residual recipient cornea encroaches upon the inserted donor implant radially towards the inside on the outside in relation to the optical axis.

A particularly preferred configuration of the control program of the computer unit for the laser system provides that the focus control brings about an undercut in the cornea which generates an incised segment that extends at least approximately radially in relation to the axis of the cornea. This radial segment generates a sealing surface which, by reason of the internal pressure within the eye, acts optimally as an annular sealing surface. The plane-parallel faces of the implant, on the one hand, and the residual cornea, on the other hand, are juxtaposed fully and over a large area under the overpressure of the eye, and the force brought about by the pressure difference is substantially perpendicular to these sealing surfaces.

The invention will be described in more detail in the following on the basis of the drawing. Shown are:

FIG. 1 schematically, a laser system for corneal grafting;

FIG. 2 a top view in the axial direction of the cornea with the path generated by the moving laser focus;

FIG. 3 a schematic axial section through the residual recipient cornea and the inserted donor implant; and FIG. 4 another exemplary embodiment of an incision shape that can be achieved with a laser system according to the invention, in a modification of the incision shape of FIG. 3.

FIG. 1 shows schematically an eye 10 and the cornea 12 thereof. In this connection it may be a question both of a recipient eye from which a central cornea segment is to be excised and of a donor eye from which a central implant for insertion into the recipient eye is to be excised. The incisions described in the following are complementary, i.e. the incision in the recipient eye for the purpose of removing the diseased or irregular corneal segment corresponds to the incision with which the implant is removed from the donor cornea.

The incision is effected by photodisruptive laser cutting, i.e. a laser beam is focused in the interior of the tissue in such a way that, by reason of its high instantaneous power, it brings about a disintegration of material (ablation) there, and the focus is then moved sequentially along a path so that, overall, an incision arises.

A laser-beam source 16 emits laser-beam pulses 18. Good results are achieved with wavelengths in the near-infrared range, in which the cornea has high permeability.

The preferred laser pulse-lengths lie within the range from 1 fs to 10 ns, and the pulse energies lie within the range from 1 nJ to 5 mJ.

By means of optical deflecting and focusing devices the laser beam 18 is focused in such a way that the focus 20 is positioned at the point where the photodisruption is to be effected—that is to say, in particular, also in the interior of the cornea, as represented schematically in FIG. 1. The optical means for controlling the position of the laser pulses and for controlling the position of the focus are represented schematically in FIG. 1 by a mirror 22 and a rerouting unit 24 and also by a lens unit 28 which brings about the focusing. The elements that are represented—that is to say, in particular, the mirror 22 and the focusing unit 28—are capable of being moved in such a way that the control, described in the following, of the path of the focus is made possible. The optical means under discussion are known as such in the state of the art and do not need to be described here in any detail. What is essential is the control of the optical means in accordance with a computer program which is saved in a computer unit 26 and which controls the computer which, in turn, drives the optical means 22, 24, 28 in accordance with the program for generating the desired focal path and therefore the desired shape of the incision.

FIG. 2 shows schematically a top view in the direction of the axis 14 of the cornea 12 and the path 30 of the foci 20 of the laser pulses 18 which is obtained by the control of the optical means. The path of the foci is rotationally symmetrical about the optical axis 14 of the cornea 12. Accordingly the laser pulses are, for example, guided around the optical axis 14 in the direction of the arrow 32, and in this way a closed orbit about the axis arises. The control of the positions of the focus in terms of depth, i.e. in the axial direction, is undertaken in accordance with the exemplary embodiments according to FIGS. 3 and 4 in such a way that an undercut arises.

FIG. 3 shows the residual part 12a of the recipient cornea and the implant part 12b of the donor cornea in the inserted state in which the healing process is to take place. In the course of excising the donor corneal segment 12b the laser system according to FIG. 1 was therefore controlled in such a way that the structure shown in FIG. 3 has arisen. The path of the incision is labelled by reference symbol 30. Correspondingly, a central segment, the shape of which corresponds to the segment 12b, has also been removed in the recipient eye.

In the exemplary embodiment according to FIG. 3 the path 30 of the foci, i.e. the line of the incision in the course of disruptive laser cutting, is angled in the manner represented—that is to say, it is zigzag-shaped in the sense that an undercut is present.

The type of incision that is represented obtains an exact centring of the donor-cornea segment 12b in the residual recipient cornea 12a. A self-sealing takes place by reason of the internal pressure P within the eye. The sealing surface is the inner segment of the incision 30 which in FIG. 3 is provided with reference symbol 34—that is to say, the so-called undercut. In the exemplary embodiment according to FIG. 3 a fixation of the implant 12b by means of a small suture will be necessary as a rule. However, this suture can be implemented in so unelaborate a manner that the problems of the state of the art outlined above are very largely avoided.

FIG. 4 shows a type of incision which has been developed further, in connection with which a fixation of the suture can be lessened still further. According to FIG. 4 the path 30 of the laser foci is zigzag-shaped in such a way that an undercut 34 arises which extends radially in relation to the optical axis 14 of the cornea. As a result, a relatively large sealing surface is obtained. The abutment surfaces arising between implant 12b and residual cornea 12a are such that the undercut 34 brings about an optimal sealing effect and positioning of the implant in interplay with the overpressure P, the direction of which in FIGS. 3 and 4 is indicated by the arrow. The presence of the undercut 34 which is radial in relation to the optical axis 14 of the cornea means that the implant 12b assumes a stable position in the residual cornea 12a, i.e. the pressure P presses the segment 12b stably (and not unstably) into a complementary recess in the residual cornea 12a.

FIG. 4 also shows the area ratios with regard to the optical zone and the so-called treatment zone. The incised optical zone 30 is so designed that the area difference between the treatment zone that is shown and the optical zone that is shown is larger than the optical zone itself. In this preferred exemplary embodiment an annular sealing surface arises (in the treatment zone outside the optical zone) with a contact force, particularly in the region of the undercut 34, that is greater than the force acting in the optical zone by reason of the internal pressure P. An example: let the optical zone have a diameter of 7 mm—that is to say, an area of about 38.5 mm$^2$. Let the treatment zone have a diameter of 10 mm—that is to say, an area of about 78.5 mm$^2$. This results in a sealing surface in the region of the undercut 34 of about 40 mm$^2$—that is to say, more than the area of the optical zone. Generally it can be deduced that it is advantageous if the sealing surface defined in the above sense (difference between the treatment zone and the optical zone according to FIG. 4) is larger than the optical zone or amounts to at least 75% thereof. An upper limit for the sealing surface is provided by the geometry of the eye itself and by a type of incision that is meaningful according to the above criteria, so that a numerical figure for this becomes superfluous.

The type of incision according to FIG. 4 permits extremely minimal suturation, which is only required to the extent that a twisting or luxation of the implant is prevented.

What is claimed is:

1. A laser system for treatment of the human eye, comprising
   a laser-beam source which emits laser pulses with wavelengths in respect of which the human cornea is transparent and with pulse-lengths within the nanosecond to femtosecond range,
   optical means for controlling the position and the focus (20) of the laser pulses and
   a computer unit which is programmed in such a manner that it controls the optical means in such a way that, in relation to an optical axis of the cornea, the foci describe a path in the interior of the cornea which is guided about the axis and which exhibits in the axial direction at least one zigzag shaped undercut with a sealing surface which corresponds to at least 75% of the area of the optical zone of the cornea.

2. Laser system according to claim 1, wherein the sealing surface is larger than the area of the optical zone of the cornea.

3. Laser system according to claim 1, wherein the wavelength lies in the near-infrared.

4. Laser system according to claim 1, wherein the laser pulse-lengths lie within the range from 1 fs to 10 ns.

5. Laser system according to claim 1, wherein the program-controlled computer unit controls the path of the foci in such a way that the undercut sealing surface extends substantially radially in relation to the optical axis of the cornea.

6. Laser system according to claim 1, wherein the program-controlled computer unit controls the path of the foci in such a way that the radial undercut ensures that an implant in the residual cornea assumes a stable position under the pressure within the eye.

7. Laser system according to claim 1, wherein the program-controlled computer unit controls the path of the foci in such a way that the radial undercut ensures that an implant in the residual cornea assume a stable position under the pressure within the eye.

8. Laser system according to claim 2, wherein the wavelength lies in the near-infrared.

9. Laser system according to claim 2, wherein the laser pulse-lengths lie within the range from 1 fs to 10 ns.

10. Laser system according to claim 2, wherein the program-controlled computer unit controls the path of the foci in such a way that the undercut sealing surface extends substantially radially in relation to the optical axis of the cornea.

11. Laser system according to claim 2, wherein the program-controlled computer unit controls the path of the foci in such a way that the radial undercut ensures that an implant in the residual cornea assume a stable position under the pressure within the eye.

12. Laser system according to claim 3, wherein the laser pulse-lengths lie within the range from 1 fs to 10 ns.

13. Laser system according to claim 3, wherein the program-controlled computer unit controls the path of the foci in such a way that the undercut sealing surface extends substantially radially in relation to the optical axis of the cornea.

14. Laser system according to claim 3, wherein the program-controlled computer unit controls the path of the foci in such a way that the radial undercut ensures that an implant in the residual cornea assume a stable position under the pressure within the eye.

15. Laser system according to claim 4, wherein the program-controlled computer unit controls the path of the foci in such a way that the undercut sealing surface extends substantially radially in relation to the optical axis of the cornea.

16. Laser system according to claim 5, wherein the program-controlled computer unit controls the path of the foci in such a way that the radial undercut ensures that an implant in the residual cornea assumes a stable position under the pressure within the eye.

17. A method for laser treatment of the human eye, comprising
providing a laser-beam source which emits laser pulses with wavelengths in respect of which the human cornea is transparent and with pulse-lengths within the nanosecond to femtosecond range, and
controlling the position and the focus of the laser pulses in such a manner in relation to an optical axis of the cornea, that the foci describe a path in the interior of the cornea which is guided about the axis and which exhibits in the axial direction at least one zigzag shaped undercut with a sealing surface which corresponds to at least 75% of the area of the optical zone of the cornea.

18. The method of claim 17, wherein said controlling includes providing a machine readable program with control instructions, and said controlling is performed in response to the machine readable program.

19. The method of claim 18, wherein the machine readable program defines the at least one zigzag shaped undercut.

20. A laser system for treatment of the human eye, comprising a laser-beam source which emits laser pulses with wavelengths in respect of which the human cornea is transparent and with pulse-lengths within the nanosecond to femtosecond range,
optical means for controlling the position and the focus of the laser pulses, and
a computer unit which is programmed in such a manner that it controls the optical means in such a way that, in relation to an optical axis of the cornea, the foci describe a path in the interior of the cornea which is guided about the axis, by which a central portion of the cornea is completely cut out axially and which exhibits in the axial direction at least one undercut with a sealing surface which corresponds to at least 75% of the area of the optical zone of the cornea.

21. Laser system according to claim 20, wherein the sealing surface is larger than the area of the optical zone of the cornea.

22. Laser system according to claim 20, wherein the undercut is zigzag-shaped.

23. Laser system according to claim 20, wherein the wavelength lies in the near-infrared.

24. Laser system according to claim 20, wherein the laser pulse-lengths lie within the range from 1 fs to 10 ns.

25. Laser system according to claim 20, wherein the program-controlled computer unit controls the path of the foci in such a way that the undercut sealing surface extends substantially radially in relation to the optical axis of the cornea.

26. Laser system according to claim 20, wherein the program-controlled computer unit controls the path of the foci in such a way that the radial undercut ensures that an implant in the residual cornea assumes a stable position under the pressure within the eye.

27. Laser system according to claim 21, wherein the undercut is zigzag-shaped.

28. Laser system according to claim 27, wherein the wavelength lies in the near-infrared.

29. Laser system according to claim 27, wherein the laser pulse-lengths lie within the range from 1 fs to 10 ns.

30. Laser system according to claim 28, wherein the laser pulse-lengths lie within the range from 1 fs to 10 ns.

31. Laser system according to claim 21, wherein the laser pulse-lengths lie within the range from 1 fs to 10 ns.

32. Laser system according to claim 21, wherein the program-controlled computer unit controls the path of the foci in such a way that the undercut sealing surface extends substantially radially in relation to the optical axis of the cornea.

33. Laser system according to claim 21, wherein the program-controlled computer unit controls the path of the foci in such a way that the radial undercut ensures that an implant in the residual cornea assumes a stable position under the pressure within the eye.

34. Laser system according to claim 22, wherein the program-controlled computer unit controls the path of the foci in such a way that the undercut sealing surface extends substantially radially in relation to the optical axis of the cornea.

35. Laser system according to claim 23, wherein the program-controlled computer unit controls the path of the foci in such a way that the undercut sealing surface (34) extends substantially radially in relation to the optical axis of the cornea.

36. Laser system according to claim 22, wherein the program-controlled computer unit controls the path of the foci in such a way that the radial undercut ensures that an implant in the residual cornea assumes a stable position under the pressure within the eye.

37. Laser system according to claim 23, wherein the program-controlled computer unit controls the path of the foci in such a way that the radial undercut ensures that an implant in the residual cornea assumes a stable position under the pressure within the eye.

38. Laser system according to claim 24, wherein the program-controlled computer unit controls the path of the foci in such a way that the radial undercut ensures that an implant in the residual cornea assumes a stable position under the pressure within the eye.

39. Laser system according to claim 25, wherein the program-controlled computer unit controls the path of the foci in such a way that the radial undercut ensures that an implant in the residual cornea assumes a stable position under the pressure within the eye.

40. A method for laser treatment of the human eye, comprising providing a laser-beam source which emits laser pulses with wavelengths in respect of which the human cornea is transparent and with pulse-lengths within the nanosecond to femtosecond range, and controlling the position and the focus of the laser pulses in such a manner in relation to an optical axis of the cornea that the foci describe a path in the interior of the cornea which is guided about the axis, by which a central portion of the cornea is completely cut out axially and which exhibits in the axial direction at least one undercut with a sealing surface which corresponds to at least 75% of the area of the optical zone of the cornea.

41. The method of claim 40, wherein said controlling includes providing a machine readable program with control instructions and said controlling is performed in response to the machine readable program.

42. The method of claim 41, wherein the machine readable program defines a substantially zigzag shaped undercut.

* * * * *